United States Patent
Kumobayashi et al.

[11] Patent Number: 5,012,002
[45] Date of Patent: Apr. 30, 1991

[54] 2,2'-BIS(DI-(M-TOLYL)PHOSPHINO)-1,1'-BINAPHTHYL

[75] Inventors: Hidenori Kumobayashi, Kanagawa; Takanao Taketomi, Chiba, both of Japan

[73] Assignee: Takasago International Corporation, Tokyo, Japan

[21] Appl. No.: 538,805

[22] Filed: Jun. 15, 1990

[30] Foreign Application Priority Data

Jun. 16, 1989 [JP] Japan .................. 1-154277

[51] Int. Cl.$^5$ .................. C07F 9/02
[52] U.S. Cl. .................. 568/17; 556/21
[58] Field of Search .................. 568/17; 552/21

[56] References Cited

U.S. PATENT DOCUMENTS

| | | | |
|---|---|---|---|
| 4,739,084 | 4/1988 | Takaya et al. | 556/21 |
| 4,739,085 | 4/1988 | Takaya et al. | 556/21 |
| 4,879,008 | 11/1989 | Puchette | 568/17 X |
| 4,879,416 | 11/1989 | Puchette et al. | 568/17 X |

Primary Examiner—Paul F. Shaver
Attorney, Agent, or Firm—Sughrue, Mion, Zinn, Macpeak & Seas

[57] ABSTRACT 2,2'-Bis[di-(m-tolyl)phosphino]-1,1'-binaphthyl represented by formula (I) is disclosed.

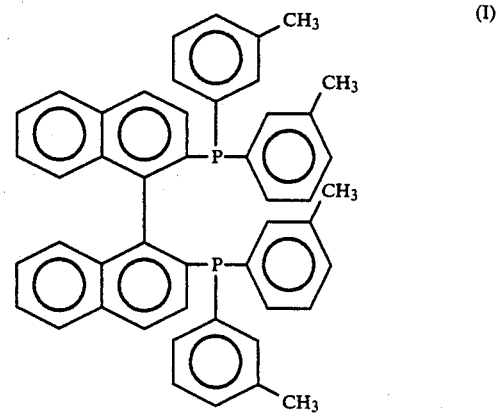

The compound of formula (I) is capable of forming a complex with a metal, e.g., ruthenium, rhodium, and palladium, which is extremely important and industrially excellent as a catalyst for various asymmetric synthesis reactions.

1 Claim, No Drawings

2,2'-BIS(DI-(M-TOLYL)PHOSPHINO)-1,1'-BINAPHTHYL

FIELD OF THE INVENTION

This invention relates to a novel phosphine compound and, more particularly to a phosphine compound capable of forming a complex with a metal, e.g., ruthenium, rhodium, and palladium, to provide a catalyst useful in various asymmetric synthesis reactions.

BACKGROUND OF THE INVENTION

Many reports have been made on transition metal catalysts useful for organic synthesis reactions, such as asymmetric hydrogenation, asymmetric isomerization, and asymmetric hydrosilylation. Among them, many of complexes in which an optically active tertiary phosphine compound is coordinated to a transition metal, e.g., ruthenium, rhodium, and palladium, exhibit excellent performance as catalysts for asymmetric synthesis reactions. To further improve the performance of these catalysts, various phosphine compounds having a special structure have hitherto been developed as disclosed, e.g., in Kacaku Sosetsu, Vol. 32, pp. 237-238, "Yuki Kinzoku Sakutai No Kagaku" (1982), edited by The Chemical Society of Japan. In particular, 2,2'-bis(diphenylphosphino)-1,1'-binaphthyl (hereinafter abbreviated as "BINAP") is one of excellent phosphine compounds. Rhodium complexes and ruthenium complexes each containing BINAP as a ligand have been reported in JP-A 55-61937 and JP-A-61-63690, respectively (the term "JP-A" as used herein means an "unexamined published Japanese patent application"). Further, it has also been reported that rhodium complexes and ruthenium complexes each using 2,2'-bis[di-(p-tolyl)phosphino]-1,1'-binaphthyl (hereinafter abbreviated as "p-T-BINAP") as a ligand give satisfactory reaction results in asymmetric hydrogenation and asymmetric isomerization as disclosed in JP-A-60-199898 and JP-A-61-63690, respectively.

While a number of special phosphine compounds have been proposed in an attempt to improve performance of complexes as catalysts for asymmetric synthesis reactions as mentioned above, the conventional catalysts are still unsatisfactory in selectivity, conversion, and durability depending on the type of the proposed reaction or reaction substrate. Hence, it has been demanded to develop a novel phosphine compound which provides a catalyst having markedly improved catalytic performance over the conventional ones.

SUMMARY OF THE INVENTION

In order to meet the above-described demand, the present inventors have conducted extensive research on various phosphine compounds. As a result, it has now been found that a BINAP derivative having a methyl group at the 3-position of the phenyl group thereof provides a metal complex catalyst having greatly improved selectivity and conversion in asymmetric syntheses as compared with conventional catalysts having BINAP with no substituent group or p-T-BINAP having a methyl group at the 4-position of the phenyl group. The present invention has been completed based on this finding.

That is, the present invention provides 2,2'-bis[di-(m-tolyl)phosphino]-1,1'-binaphthyl (hereinafter abbreviated as "m-T-BINAP") represented by formula (I):

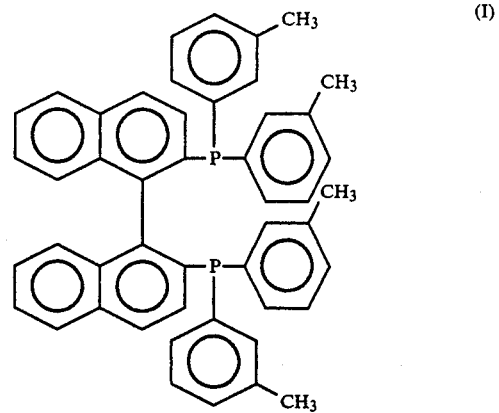

For the compound of formula (I), there are (+)- and (−)-optically active isomers, and the present invention embraces both of these isomers and a racemate thereof.

The compound of formula (I) can be prepared through, for example, the following reaction scheme:

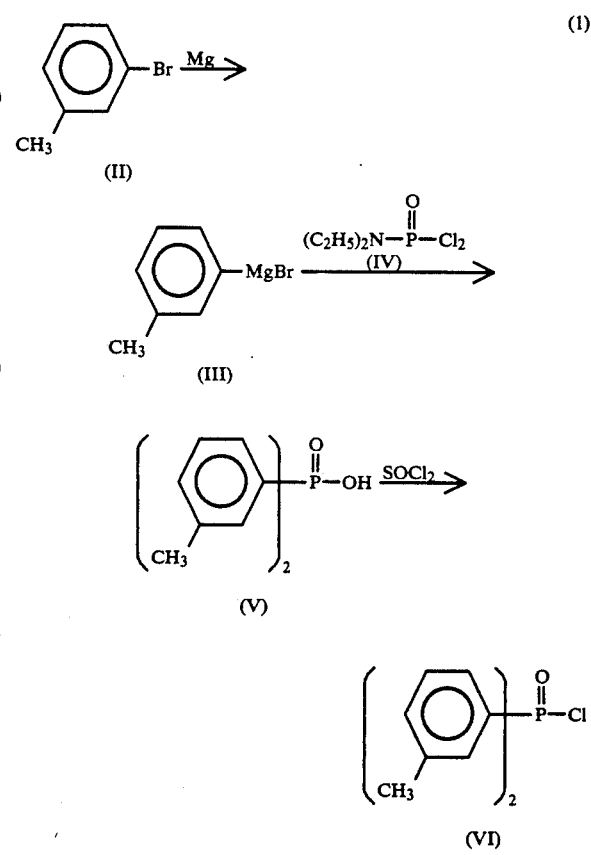

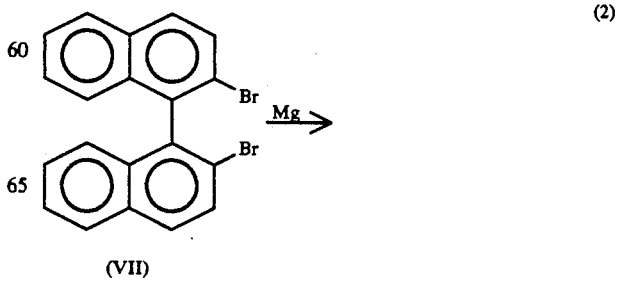

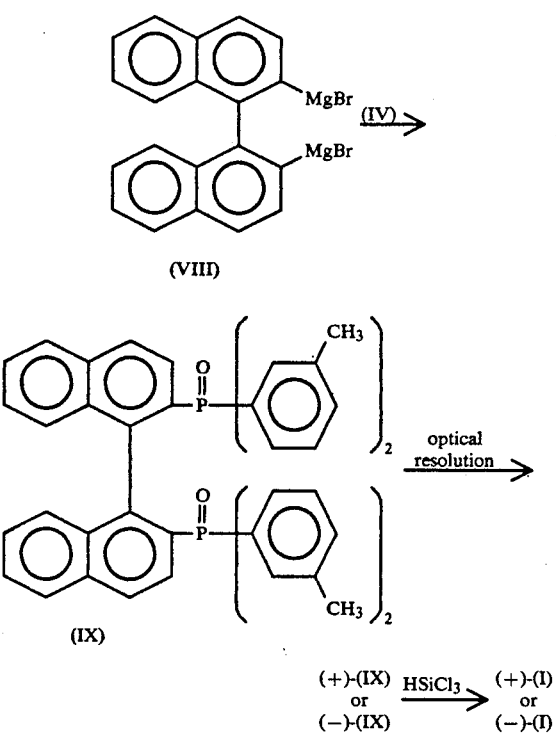

That is, m-bromotoluene (II) is reacted with metallic magnesium to prepare a Grignard reagent (III) which is then condensed with N,N-diethylamidochlorophosphate (IV) obtained by the process described in G. M. Kosolapoff et al., *J. Am. Chem. Soc.*, Vol. 71, pp. 369-370 (1949), followed by hydrolysis with hydrochloric acid to obtain di-(m-tolyl)phosphinic acid (V). The compound (V) is reacted with thionyl chloride. After removing excess thionyl chloride, the reaction mixture is recrystallized from a mixed solution of benzene and hexane to obtain di-(m-tolyl)phosphonyl chloride (VI).

Separately, 2,2'-dibromo-1,1'-binaphthyl (VII) obtained by the process disclosed in JP-A-55-61937 is reacted with metallic magnesium to prepare a Grignard reagent (VIII) which is then reacted with the above prepared compound (VI) to synthesize 2,2'-bis[di-(m-tolyl)phosphoryl]-1,1'-binaphthyl (IX). The thus obtained racemic compound (IX) is optically resolved by using an optically active column, followed by reduction with trichlorosilane to obtain a (+)-isomer or a (−)-isomer of the compound (I).

The compound (I) according to the present invention forms a complex with a transition metal, e.g., ruthenium. For example, [RuCl$_2$(p-cymene)]$_2$ which is prepared by the process described in M. A. Bennett, *J. Chem. Soc. Dalton*, pp. 233-241 (1974) is treated with potassium iodide in the presence of a phase transfer catalyst (e.g., tetramethylammonium iodide) to obtain [RuI$_2$(p-cymene)]$_2$ which is then reacted with the compound of formula (I) (m-T-BINAP) to obtain [RuI(p-cymene)(m-T-BINAP)]I.

The thus obtained complex can be used as a catalyst for asymmetric synthesis reactions, such as asymmetric hydrogenation of β-keto esters, to produce reduction products of high optical purity in high optical yield. Further, a reduction product having a desired absolute configuration can be obtained by appropriately selecting the absolute configuration of the compound (I), i.e., a (+)-isomer or a (−)-isomer, as a ligand for complex formation.

The present invention is now illustrated in greater detail with reference to Examples, but it should be understood that the present invention is not construed as being limited thereto. All the parts, percents, and ratios are by weight unless otherwise indicated.

Measuring equipment used in a Examples are as follows.

Melting Point: Micro melting point measuring apparatus (manufactured by Yanagimoto Seisakusho K. K.)

NMR: Model AM-400 (400 MHz) (manufactured by Bruker Inc.)

Internal Standard:
$^1$H-NMR: tetramethylsilane
External Standard:
$^{31}$P-NMR: 85% phosphoric acid Optical Rotation: Model DIP-4 (manufactured by Nippon Bunko Kogyo K. K.)

Optical Purity:
High Performance Liquid Chromatography (HPLC): Hitachi Liquid Chromatograph L-6000 (produced by Hitachi, Ltd.)

Detector: UV Detector L-4000 (manufactured by Hitachi, Ltd.)

EXAMPLE 1

(a) Preparation of Di-(m-tolyl)phosphinic acid (V)

In 250 ml of dehydrated diethyl ether, 102.6 g (0.6 mole) of m-bromotoluene was reacted with 15.3 g (0.64 mole) of metallic magnesium to prepare a Grignard reagent. To the resulting Grignard reagent was added dropwise 57 g (0.3 mole) of N,N-diethylamidochlorophosphate at 37° to 38° C. over a period of 2 hours. After the reaction mixture was heated at reflux for 4.5 hours, 400 ml of ice-water and 150 ml of saturated aqueous ammonium chloride were added thereto to decompose the salt. After liquid separation, 400 ml of concentrated hydrochloric acid was added to the ether layer under ice-cooling, followed by heating to remove the ether by distillation. To the residue was further added 100 ml of concentrated hydrochloric acid, and a reaction was conducted at 100° to 110° C. for 5 hours. The formed oily substance was separated from the aqueous layer, and 50 ml of a 20% aqueous solution of sodium hydroxide was added thereto to form a uniform solution. The insoluble matter was removed by extraction with toluene, and 20% sulfuric acid was added to the solution to neutralize and further to make it acidic. The precipitate thus formed was collected by filtration, washed with water, and dried to obtain 27 g of a crude product. Recrystallization from methanol yielded 25.4 g (percent yield: 34%) of di-(m-tolyl)phosphinic acid as a colorless solid having a melting point of 171.5° C.

(b) Preparation of Di-(m-tolyl)phosphonyl chloride (VI)

In 200 ml of benzene was suspended 52.5 g (0.214 mole) of di-(m-tolyl)phosphinic acid, and 28 g (0.235 mole) of thionyl chloride was added dropwise to the suspension at 45° C. The mixture was heated up to 62° C. and refluxed for 2 hours. After the reaction, excess thionyl chloride was removed at a bath temperature of 60° C. under reduced pressure, and the reaction mixture was distilled in a high degree of vacuum (0.25 mmHg)

to obtain 52.3 g (percent yield: 92.5%) of di-(m-tolyl)-phosphonyl chloride.

(c) Preparation of 2,2'-Bis[di-(m-tolyl)phosphoryl]-1,1'-binaphthyl (IX)

55.1 g (0.12 mole) of 2,2'-dibromo-1,1'-binaphthyl (purity: 90%) was reacted with 6.33 g (0.264 mole) of metallic magnesium in 100 ml of toluene and 100 ml of tetrahydrofuran to prepare a Grignard reagent. To the resulting Grignard reagent was added 50 ml of a toluene solution containing 66.9 g (0.25 mole) of di-(m-tolyl)-phosphonyl chloride, and the mixture was allowed to react at 45° C. After adding 200 ml of water, the reaction mixture was extracted thrice with 100 ml portions of dichloroethane. After liquid separation, the solvent was removed by distillation, and the resulting concentrate was recrystallized from a 7:3 (by volume) mixture of dichloroethane and toluene to obtain 58.5 g of a primary crystal (melting point: 311°–316° C.) and 18.1 g of a secondary crystal (melting point: 310°–315° C.), totaling 76.6 g (percent yield: 89.8%). The primary and secondary crystals combined were identified to be the entitled compound by $^1$H-NMR.

$^1$H-NMR (CDCl$_3$) ⊕ (ppm): 2.091 (s, 6 H), 2.198 (s, 6 H), 6.89–7.82 (m, 28 H).

(d) Optical Resolution of 2,2'-Bis[di-(m-tolyl)phosphoryl]-1,1'-binaphthyl (IX)

One gram of the racemic compound as obtained in (c) above was subjected to HPLC under conditions shown below to obtain 0.4 g (percent yield: 80%) of one of the enantiomers.

Column: Optically active column for semi-fractionation Chiral Cell OG (1 cm (d) ×25 cm (h)), manufactured by Daicel Chemical Industries, Ltd.

Developing Solvent: Hexane:isopropanol=95:5 (by volume); flow rate: 0.4 ml/min

UV Detection Wavelength: 270 nm

The optical purity of the thus recovered isomer was found to be 99.89% ee by HPLC under conditions shown below.

Column: Chiral Pack OP (0.46 cm (d) ×25 cm (h)), manufactured by Daicel Chemical Industries, Ltd.

Developing Solvent: Methanol; flow rate: 1 ml/min

UV Detection Wavelength: 254 nm (e) Preparation of (+)-2,2'-Bis[di-(m-tolyl)phosphino]-1,1-binaphthyl (I)

To 0.4 g (0.56 mmole) of the optically active compound (IX) obtained in (d) above were added 20 ml of xylene and 1.13 g (11.2 mmole) of triethylamine, and the mixture was stirred to form a solution. To the solution was added dropwise 1.51 g (11.2 mmole) of trichlorosilane over a period of 20 to 30 minutes, and the mixture was allowed to react at 100° C. for 1 hour, then at 120° C. for 1 hour, and finally at 140° C. for 1 hour. After cooling to room temperature, 5 ml of a 30% aqueous sodium hydroxide solution was added thereto, and the mixture was stirred at 50° to 60° C. for 30 minutes, followed by liquid separation. The xylene layer was concentrated, and degassed methanol was added to the residue to effect recrystallization. There was obtained 0.349 g (percent yield: 92%) of (+)-2,2'-bis[di-(m-tolyl)-phosphino]-1,1'-binaphthyl.

Melting Point: 179°–182° C.

$[\alpha]_D^{25}$: +234.1° (c=1.0, benzene).

$^1$H-NMR (CDCl$_3$) δ (ppm): 2.10 (s, 6 H), 2.129 (s, 6 H), 6.79–7.87 (m, 28 H).

(f) Preparation of (−)-2,2'-Bis[di-(m-tolyl)phosphino]-1,1'-binaphthyl 0.31 g (0.437 mmole) of the other optical isomer (IX) obtained in (d) was treated in the same manner as in (e) to obtain 0.267 g (percent yield: 90%) of (−)-2,2'-bis[di-(m-tolyl)phosphino]-1,1'-binaphthyl.

Melting Point: 150°14 182° C.

$[\alpha]_D^{25}$: −232.4° (c=1.0, benzene).

A complex was prepared by using the compound (I) of the present invention according to Reference Example described below, and asymmetric hydrogenation was conducted using the resulting complex as a catalyst in Test Example 1. For comparison, asymmetric hydrogenation was conducted using conventional catalysts in Comparative Test Examples 1 to 2.

REFERENCE EXAMPLE

Preparation of [RuI(p-cymene)(m-T-BINAP)]I

In a mixed solvent of 50 ml of water and 50 ml of methylene chloride were dissolved 2 g (3.27 mmole) of [RuCl$_2$(p-cymene)]$_2$, 1.8 g (10.84 mmole) of potassium iodide, and 0.07 g (0.35 mmole) of tetramethylammonium iodide, and the solution was stirred at room temperature for 4 hours. The aqueous phase was removed by liquid separation, and the residual phase was washed with 50 ml of water and then distilled under reduced pressure (20 mmHg) to remove the methylene chloride. The residue was dried at room temperature in a high degree of vacuum (0.2 mmHg) to obtain 3.03 g (percent yield: 95%) of a reddish brown complex [RuI$_2$(p-cymene)]$_2$.

$^1$H-NMR (CD$_2$Cl$_2$) δ (ppm): 1.25 (d, 6 H, J=6.93 Hz), 2.35 (s, 3 H), 3.00 (d-t, 1 H, J=6.93 Hz), 5.42 (d, 2 H, J=5.96 Hz), 5.52 (d, 2 H, J=5.96 Hz).

In a mixed solvent of 45 ml of ethanol and 23 ml of methylene chloride were dissolved 0.248 g (0.264 mmole) of the resulting complex and 0.358 g (0.528 mmole) of (+)-m-T-BINAP, and the solution was allowed to react at 50° C. for 1 hour. The reaction mixture was concentrated to dryness to quantitatively give 0.613 g of the entitled complex.

Elemental Analysis for C$_{58}$H$_{54}$P$_2$Ru: Calcd. (%): C 59.64; H 4.63; Found (%): C 59.95; H 4.74.

$^{31}$P-NMR (CD$_2$Cl$_2$) δ (ppm): 23.46 (d, J=59.7 Hz), 39.28 (d, J=59.5 Hz).

TEST EXAMPLE 1

Asymmetric hydrogenation of methyl 2-benzamidomethyl-3-oxobutanoate

In a 200 ml stainless steel-made autoclave whose atmosphere had been displaced with nitrogen were charged 15 g (0.06 mole) of methyl 2-benzamidomethyl-3-oxobutanoate, 75 ml of methanol, and 70 mg (0.06 mmole) of [RuI(p-cymene)((−)-m-T-BINAP)]I, and hydrogenation reaction was carried out at 50° C. and at a hydrogen pressure of 50 kg/cm$^2$ for 20 hours. After the reaction, the solvent was removed by distillation to obtain 15.1 g of a hydrogenation product. Two major products were obtained by silica gel column chromatography (hexane: isopropanol=85:15 by volume). On structural analysis by $^1$H-NMR, it was confirmed that two diastereomers (designated component A and component B) had been formed.

$^1$H-NMR (CDCl$_3$) δ (ppm): Component A: 1.26 (d, 3 H, J=6.25 Hz), 2.60–2.64 (m, 1 H), 3.57–3.62 (m, 1 H), 4.00–4.03 (m, 1 H), 3.73 (s, 3 H), 4.08–4.14 (m, 1 H), 7.27

(br. s, 1 H), 7.41–7.45 (m, 2 H), 7.49–7.53 (m, 1 H), 7.77–7.80 (m, 1 H). Component B: 1.30 (d, 3 H, J=6.28 Hz), 2.84–2.86 (m, 1 H), 3.74 (s, 3 H), 3.71–3.77 (m, 1 H), 3.85–3.91 (m, 1 H), 4.09–4.14 (m, 1 H), 6.92 (br, s, 1 H), 7.40–7.44 (m, 2 H), 7.48–7.50 (m, 1 H), 7.74–7.76 (m, 1 H).

The conversion and the production ratio of components A and B were determined by HPLC under the following conditions:

Column: Develosil 60-5 (4.6 mm (d)×250 mm (h)), produced by Nomura Chemical Co., Ltd.

Eluent: Hexane:chloroform:methanol=900:100:20 by volume; flow rate: 2.5 ml/min

UV Detection Wavelength: 254 nm

As a result, the conversion was 94%, and the A/B production ratio was 83.5/16.5.

Further, each component isolated by silica gel column chromatography (hexan:ethyl acetate=1:1 by volume) was converted to a methoxytrifluoromethylphenylacetic acid ester and analyzed by HPLC under the following conditions:

Column: Chiral Cell OD (0.46 cm (d) ×25 cm (h)), produced by Daicel Chemical Industries, Ltd.

Eluent: Hexane:isopropanol=9:1 by volume; flow rate: 1 ml/min

UV Detection Wavelength: 254 nm

As a result, the optical purity of components A and B was found to be 95% ee and 92% ee, respectively.

COMPARATIVE TEST EXAMPLE 1

In a 200 ml autoclave whose atmosphere had been displaced with nitrogen were charged 15 g (0.06 mole) of methyl 2-benzamidomethyl-3-oxobutanoate, 75 ml of methanol, and 50.6 mg (0.03 mmole) of $Ru_2Cl_4((-)-BINAP)_2(C_2H_5)_3N$, and hydrogenation reaction was conducted at 50° C. and at a hydrogen pressure of 50 kg/cm$^2$ for 20 hours.

Analyses made of the reaction product in the same manner as in Test Example 1 revealed that the conversion was 80%; the A/B production ratio was 53/47; and the optical purity of components A and B were 94% ee and 93.5% ee, respectively.

COMPARATIVE TEST EXAMPLE 2

In a 200 ml autoclave whose atmosphere had been displaced with nitrogen were charged 15 g (0.06 mole) of methyl 2-benzamidomethyl-3-oxobutanoate, 75 ml of methanol, and 54 mg (0.03 mmole) of $Ru_2Cl_4((-)-p-T-BINAP)_2(C_2H_5)_3N$, and hydrogenation reaction was conducted at 50° C. and at a hydrogen pressure of 50 kg/cm$^2$ for 20 hours.

Analyses made in the same manner as in Test Example 1 revealed that the conversion was 65%; the A/B production ratio was 65/35; and the optical purity of components A and B were 94% ee and 93.8% ee, respectively.

As described above, the novel phosphine compound according to the present invention is capable of forming a complex with a metal, e.g., ruthenium, rhodium, and palladium, which is extremely important and industrially excellent as a catalyst for various asymmetric synthesis reactions.

While the invention has been described in detail and with reference to specific embodiments thereof, it will be apparent to one skilled in the art that various changes and modifications can be made therein without departing from the spirit and scope thereof.

What is claimed is:

1. 2,2'-Bis[di-(m-tolyl)phosphino]-1,1'-binaphthyl represented by formula (I):

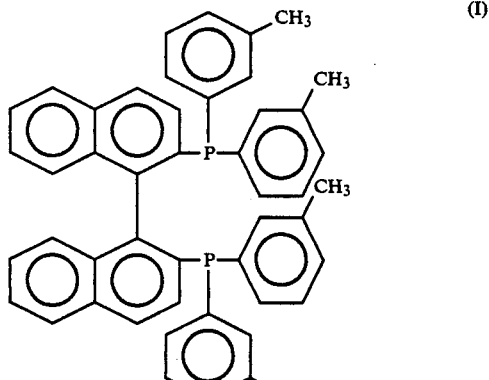

* * * * *